(12) United States Patent
Gleich et al.

(10) Patent No.: US 8,179,131 B2
(45) Date of Patent: May 15, 2012

(54) METHOD AND ARRANGEMENT FOR INFLUENCING AND/OR DETECTING MAGNETIC PARTICLES IN A REGION OF ACTION BY ROTATING MAGNETIC DRIVE VECTOR

(75) Inventors: Bernhard Gleich, Hamburg (DE); Juergen Weizenecker, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 383 days.

(21) Appl. No.: 12/519,783

(22) PCT Filed: Dec. 17, 2007

(86) PCT No.: PCT/IB2007/055177
§ 371 (c)(1),
(2), (4) Date: Jun. 18, 2009

(87) PCT Pub. No.: WO2008/078275
PCT Pub. Date: Jul. 3, 2008

(65) Prior Publication Data
US 2010/0102805 A1    Apr. 29, 2010

(30) Foreign Application Priority Data
Dec. 20, 2006 (EP) .................................... 06126574

(51) Int. Cl.
*G01N 27/72* (2006.01)
*G01R 33/12* (2006.01)
(52) U.S. Cl. ........... 324/228; 324/243; 600/12; 128/899
(58) Field of Classification Search .................. 324/228, 324/243; 600/12; 128/899
See application file for complete search history.

(56) References Cited

U.S. PATENT DOCUMENTS

| | | | | |
|---|---|---|---|---|
| 4,639,674 A | * | 1/1987 | Rippingale | 324/326 |
| 4,878,023 A | * | 10/1989 | Overweg et al. | 324/318 |
| 7,167,004 B1 | * | 1/2007 | Kruip | 324/320 |
| 2001/0031906 A1 | * | 10/2001 | Ishikawa et al. | 600/13 |
| 2003/0085703 A1 | * | 5/2003 | Gleich | 324/309 |

FOREIGN PATENT DOCUMENTS

| | | |
|---|---|---|
| DE | 10151778 | 5/2003 |
| WO | W02004091386 | 10/2004 |
| WO | W02004091390 | 10/2004 |
| WO | W02005121838 | 12/2005 |

OTHER PUBLICATIONS

Kahler, et al., "Rotational Magnetization Measurements on Magnetic Particle Recording Tape", Physica B Elsevier Netherlands, vol. 343, No. 1-4, Jan. 1, 2004, pp. 350-356, XP002482904.

* cited by examiner

Primary Examiner — Jay Patidar

(57) ABSTRACT

A method for influencing and/or detecting magnetic particles in a region of action includes generating a magnetic selection field having a pattern in space of its magnetic field strength such that a first sub-zone having a low magnetic field strength and a second sub-zone having a higher magnetic field strength are formed in the region of action. The method further includes changing the position in space of the two sub-zones in the region of action by means of a magnetic drive field so that the magnetization of the magnetic particles change locally, and acquiring signals that depend on the magnetization in the region of action. The magnetization is influenced by the change in the position in space of the first and second sub-zone. The magnetic drive vector of the magnetic drive field is rotated in at least one rotation plane.

15 Claims, 3 Drawing Sheets

METHOD AND ARRANGEMENT FOR INFLUENCING AND/OR DETECTING MAGNETIC PARTICLES IN A REGION OF ACTION BY ROTATING MAGNETIC DRIVE VECTOR

CROSS REFERENCE TO RELATED APPLICATIONS

This application claims the benefit of EP provisional application s/n 06126574.0, filed Dec. 20, 2006, which is incorporated herein by reference. Related applications are: PCT s/n IB2007/055126, "Arrangement and Method for Influencing and/or Detecting Magnetic Particles in a Region of Action," filed Dec. 14, 2007, PCT s/n IB2007/055152, "Arrangement for Influencing and/or Detecting Magnetic Particles in a Region of Action and Method of Producing a Disk Shaped Coil," filed Dec. 17, 2007, PCT s/n IB2007/055157, "Arrangement and Method for Influencing and/or Detecting Magnetic Particles in a Region of Action," filed Dec. 17, 2007, PCT s/n IB2007/055134, "Arrangement and Method for Influencing and/or Detecting Magnetic Particles in a Region of Action," filed Dec. 14, 2007, PCT s/n IB2007/055174, "Arrangement and Method for Influencing and/or Detecting Magnetic Particles in a Region of Action," filed Dec. 17, 2007, PCT s/n IB2007/055131, "Arrangement and Method for Influencing and/or Detecting Magnetic Particles in a Region of Action," filed Dec. 14, 2007, PCT s/n IB2007/055158, "Arrangement and Method for Influencing and/or Detecting and/or Locating Magnetic Particles in a Region of Action," filed Dec. 17, 2007, PCT s/n IB2007/055162, "Method and Arrangement for Locating Magnetic Markers in a Region of Action," filed Dec. 17, 2007, PCT s/n IB2007/055178, "Arrangement and Method for Detecting and/or Locating a Magnetic Material in a Region of Action, Use of a Arrangement In the Examination of Buildings," filed Dec. 17, 2007, PCT s/n IB2007/055204, "Method and Arrangement for Separating Magnetic Particles, Magnetic Particles and Use of Magnetic Particles," filed Dec. 18, 2007, PCT s/n IB2007/055165, "Arrangement and Method for Influencing and/or Detecting Magnetic Particles in a Region of Action, Coil Arrangement," filed Dec. 17, 2007, and PCT s/n IB2007/055163, "Influencing and/or Detecting Magnetic Particles in a Region of Action of a Examination Object," filed Dec. 17, 2007.

The present invention relates to a method for influencing and/or detecting magnetic particles and to the use of magnetic particles. Furthermore, the invention relates to an arrangement for influencing and/or detecting magnetic particles in a region of action.

A method of such a kind is known from German Patent Application DE 101 51 778 A1. In the case of the method described in that publication, first of all a magnetic field having a spatial distribution of the magnetic field strength is generated such that a first sub-zone having a relatively low magnetic field strength and a second sub-zone having a relatively high magnetic field strength are formed in the examination zone. The position in space of the sub-zones in the examination zone is then shifted, so that the magnetization of the particles in the examination zone changes locally. Signals are recorded which are dependent on the magnetization in the examination zone, which magnetization has been influenced by the shift in the position in space of the sub-zones, and information concerning the spatial distribution of the magnetic particles in the examination zone is extracted from these signals, so that an image of the examination zone can be formed. Such an arrangement and such a method have the advantage that it can be used to examine arbitrary examination objects—e.g. human bodies—in a non-destructive manner and without causing any damage and with a high spatial resolution, both close to the surface and remote from the surface of the examination object.

The performance of such known arrangement depend strongly on the performance of the tracer material, i.e. the material of the magnetic particles. Because the signal-to-noise ratio of known arrangements and with conventional drive sequences is comparably low, there exists the need for an enhanced signal-to-noise ratio.

It is therefore an object of the present invention to provide a method in which the drawbacks of the prior art are avoided or at least reduced.

The above object is achieved by a method for influencing and/or detecting magnetic particles in a region of action, wherein the method comprises the steps of generating a magnetic selection field having a pattern in space of its magnetic field strength such that a first sub-zone having a low magnetic field strength and a second sub-zone having a higher magnetic field strength are formed in the region of action, furthermore changing the position in space of the two sub-zones in the region of action by means of a magnetic drive field so that the magnetization of the magnetic particles change locally, furthermore acquiring signals, which signals depend on the magnetization in the region of action, which magnetization is influenced by the change in the position in space of the first and second sub-zone, wherein a magnetic drive vector, i.e. the vector of the magnetic field strength of the magnetic drive field, is rotated in at least one rotation plane.

The advantage of such a method is that it is possible to achieve a higher signal-to-noise ratio because a higher signal to noise ratio can be reached when the magnetic drive vector has a special angular relationship with the easy axis of an anisotropic magnetic particle. By rotating the magnetic drive vector in a plane and with the presence of magnetic particles having an anisotropy of their magnetization, it is possible that—in a first step—the magnetic particles are oriented with their easy axis (or axis of easy magnetization) along a preferred orientation more or less parallel to the magnetic drive vector at that moment and that—in a second step—the magnetization of the magnetic particles is then changed (or reversed) by means of the drive vector being meanwhile rotated and directing in a direction enclosing a relatively great angle with the former direction, i.e. with the mean direction of the easy axis of the magnetic particles. The direction of the magnetic drive vector in the first step is hereinafter called the first direction. The direction of the magnetic drive vector in the second step is hereinafter called the second direction. The first and second direction enclose a special angle which is preferably in the range of about 40 to 50 degrees. As the magnetic particles form a statistical set of small particles subjected to thermal movement, it is evident that not all magnetic particles precisely behave as described. According to the present invention, it is therefore preferred that inside the field of view, i.e. inside the region where the comparably quickly changing magnetic drive field interacts with the magnetic particles, for at least 50% of the magnetic particles the easy axis is oriented in a solid angle of at most $\pi/2$ around the first direction and for at least 30% of the time of the applied sequence of movement of the magnetic drive vector. Furthermore, it is preferred that—at least for certain parts of the field of view—at least 20% of the magnetization reversals of the magnetic particles are induced by a magnetic drive field (i.e. a magnetic drive vector) being directed in a direction differing at least 20 degrees and at most 70 degrees from the first direction (i.e. the mean direction of the easy axis of the particles). Furthermore, it is preferred that—at least for certain parts of the field of view—at least 50% of the magnetization reversals of the magnetic particles are induced by a magnetic drive field being directed in a direction differing at least 30 degrees and at most 60 degrees from the first direction.

According to a preferred embodiment of the present invention, the rotation of the magnetic drive vector of the magnetic drive field is performed continuously during the acquisition of the signals. Thereby, it is advantageously possible to continuously provide the special angular relationship of the magnetic drive vector and the easy axis of an anisotropic magnetic particle, thereby enhancing the signal-to-noise ratio in the acquisition of signals.

Furthermore, it is preferred according to the present invention that the plane of rotation of the magnetic drive vector of the magnetic drive field is also rotated during the rotation of the magnetic drive vector of the magnetic drive field. Thereby, it is advantageously possible not to prefer one plane in the detection of the magnetic particles but to perform the detection of the magnetic particles in a symmetric manner.

In a further embodiment of the present invention, it is preferred that the rotation of the magnetic drive vector of the magnetic drive field is made at a frequency of about 100 Hz to about 100 kHz. Thereby, it is possible to use the inventive method in a very flexible manner and to adapt the inventive method to a plurality of different particles and to a plurality of different environments of the magnetic particles.

According to a preferred embodiment of the present invention, the frequency of the rotation of the magnetic drive vector of the magnetic drive field is in the range of the frequency of rotation of the magnetic particles in their environment. Thereby, it is possible to provide the special angular relationship of the magnetic drive vector and the easy axis of an anisotropic magnetic particle in a particularly simple manner.

Furthermore, it is preferred according to the present invention that the frequency of the rotation of the magnetic drive vector of the magnetic drive field is changed such that the signal to noise ratio of the acquired signal is optimal. Thereby, it is advantageously possible to perform a calibration step in the inventive method, especially before acquiring a large number of signals related to the magnetic particles. If the frequency of rotation of the magnetic particles or at least a part of the magnetic particles is at least approximately known or not known at all, the frequency of rotation of the drive vector of the magnetic drive field can then be varied on a smaller or larger range corresponding to the rotational mobility of the magnetic particles such that the signal to noise ratio is optimal.

Still furthermore it is preferred according to the present invention that magnetic particles are used having a strength of anisotropy of their magnetization, the strength of anisotropy of the magnetization preferably being in the range of about 1 mT to about 10 mT, very preferably in the range of about 3 mT to about 5 mT. Thereby, it is advantageously possible to enhance the signal to noise ratio of the signals acquired in respect of such magnetic particles relative to magnetic particles having a smaller or a greater strength of anisotropy of their magnetization. In the context of the present invention, the term "strength of anisotropy of the magnetization of magnetic particles" signifies the exterior magnetic field (exterior relative to the magnetic particle or particles) that is necessary in order to change significantly the magnetization of the magnetic particle or particles. This interpretation is strongly correlated to other definitions relatable to the term "anisotropy of magnetic particles" or "field of anisotropy", e.g. different energies related to different spatial directions (energy landscape) expressed by means of a plurality of constants of anisotropy. In the context of the present invention, the term "strength of anisotropy of the magnetization of magnetic particles" is related to a quantifiable parameter.

According to further embodiments of the present invention, the anisotropy of the magnetization is due to shape anisotropy and/or crystal anisotropy and/or induced anisotropy and/or surface anisotropy. Thereby, a large choice of possible magnetic particles is available when using such magnetic particles in accordance with the present invention.

Furthermore, it is preferred according to the present invention that the rotation of the magnetic drive vector of the magnetic drive field is performed such that the magnetic drive vector of the magnetic drive field is oriented with a relatively high probability in an angle relative to the direction of easy magnetization of the magnetic particles. Thereby, the best signal to noise ratio can be reached. According to the present invention, the angle is preferably in the range of about 20° to about 70°, very preferably in the range of about 30° to about 60°, most preferably in the range of about 40° to about 50°, still most preferably of about 45°.

The invention further relates to an arrangement for influencing and/or detecting magnetic particles in a region of action, which arrangement comprises selection means for generating a magnetic selection field having a pattern in space of its magnetic field strength such that a first sub-zone having a low magnetic field strength and a second sub-zone having a higher magnetic field strength are formed in the region of action, furthermore drive means for changing the position in space of the two sub-zones in the region of action by means of a magnetic drive field so that the magnetization of the magnetic particles changes locally, furthermore receiving means for acquiring signals, which signals depend on the magnetization in the region of action, which magnetization is influenced by the change in the position in space of the first and second sub-zone, wherein a magnetic drive vector of the magnetic drive field is rotated in at least one rotation plane.

With the inventive arrangement, it is advantageously possible to provide measurements of the location and/or the distribution of the magnetic particles in a region of action with a higher precision due to a higher signal to noise ratio. Preferably, rotation of the magnetic drive vector of the magnetic drive field is made at a frequency of about 100 Hz to about 100 kHz.

The invention further relates to a computer program for an inventive arrangement for carrying out the inventive method and to a computer program product comprising such a computer program.

The present invention is also related to the use of magnetic particles having a strength of anisotropy of the magnetization in the range of about 1 mT to about 10 mT, preferably about 3 mT to about 5 mT. With such particles, it is possible to enhance the signal to noise ration in the application of magnetic particle imaging provided that the external magnetic field that is experienced by the particles is oriented in a specific range of angles relative to the direction of the easy magnetization (easy axis) of the magnetic particles. Generally according to the present invention, i.e. in the context of magnetic particle imaging, it is preferred to use larger particles as they potentially have a larger possible magnetization which in turn can lead to a higher signal-to-noise ratio at the detection stage. Nevertheless, the size of the magnetic particles is limited because larger particles attract each other due to their magnetic moment and form cluster of magnetic particles, invisible to the method of magnetic particle imaging. According to the invention, small particles of well defined strength of anisotropy of their magnetization are suggested which behave like larger magnetic particles, i.e. which behave like particles of e.g. the double volume and therefore a sharper magnetization step.

The magnetic field strength mentioned in the context of the present invention can also be specified in tesla. This is not correct, as tesla is the unit of the magnetic flux density. In order to obtain the particular magnetic field strength, the value specified in each case still has to be divided by the magnetic field constant $\mu g_0$.

According to the present invention, it is to be understood that the selection means and/or the drive means and/or the receiving means can at least partially be provided in the form of one single coil or solenoid. However, it is preferred according to the present invention that separate coils are provided to form the selection means, the drive means and the receiving means. Furthermore according to the present invention, the selection means and/or the drive means and/or the receiving means can each be composed of separate individual parts, especially separate individual coils or solenoids, provided and/or arranged such that the separate parts form together the selection means and/or the drive means and/or the receiving means. Especially for the drive means and/or the selection means, a plurality of parts, especially pairs for coils (e.g. in a Helmholtz or Anti-Helmholtz configuration) are preferred in order to provide the possibility to generate and/or to detect components of magnetic fields directed in different spacial directions.

These and other characteristics, features and advantages of the present invention will become apparent from the following detailed description, taken in conjunction with the accompanying drawings, which illustrate, by way of example, the principles of the invention. The description is given for the sake of example only, without limiting the scope of the invention. The reference figures quoted below refer to the attached drawings.

Figure 1:
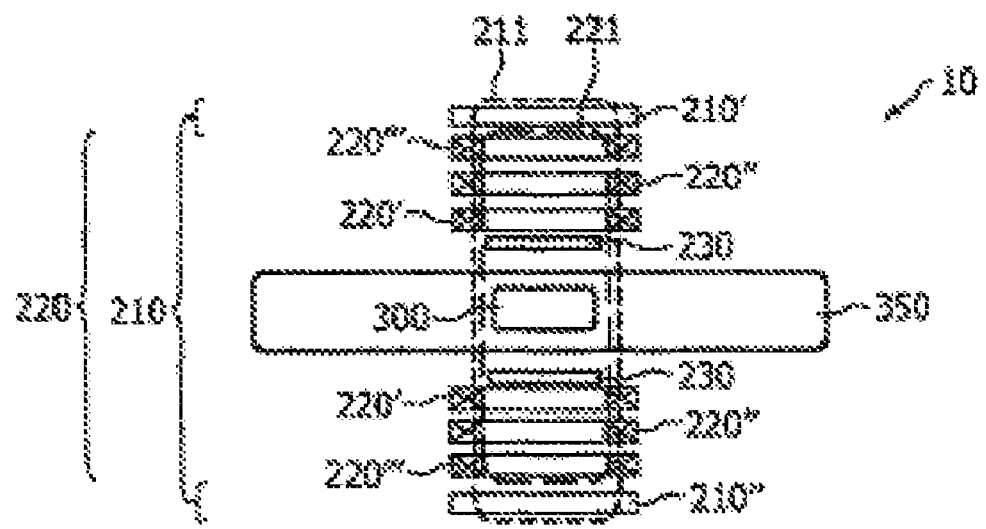
FIG. 1 illustrates an arrangement according to the present invention for carrying out the method according to the present invention.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes.

Where an indefinite or definite article is used when referring to a singular noun, e.g. "a", "an", "the", this includes a plural of that noun unless something else is specifically stated.

Furthermore, the terms first, second, third and the like in the description and in the claims are used for distinguishing between similar elements and not necessarily for describing a sequential or chronological order. It is to be understood that the terms so used are interchangeable under appropriate circumstances and that the embodiments of the invention described herein are capable of operation in other sequences than described of illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the present description and claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

In FIG. 1, an arbitrary object to be examined by means of an arrangement 10 according to the present invention is shown. The reference numeral 350 in FIG. 1 denotes an object, in this case a human or animal patient, who is arranged on a patient table, only part of the top of which is shown. Prior to the application of the method according to the present invention, magnetic particles 100 (not shown in FIG. 1) are arranged in a region of action 300 of the inventive arrangement 10. Especially prior to a therapeutical and/or diagnostical treatment of, for example, a tumor, the magnetic particles 100 are positioned in the region of action 300, e.g. by means of a liquid (not shown) comprising the magnetic particles 100 which is injected into the body of the patient 350.

Figure 2:
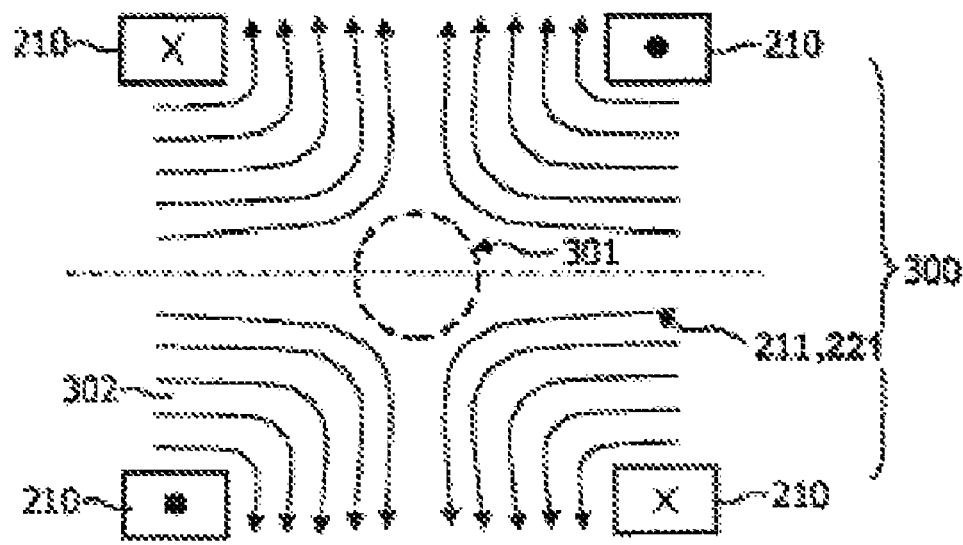
FIG. 2 illustrates an example of the field line pattern produced by an arrangement according to the present invention

As an example of an embodiment of the present invention, an arrangement 10 is shown in FIG. 2 comprising a plurality of coils forming a selection means 210 whose range defines the region of action 300 which is also called the region of examination 300. For example, the selection means 210 is arranged above and below the object 350. For example, the selection means 210 comprise a first pair of coils 210', 210", each comprising two identically constructed windings 210' and 210" which are arranged coaxially above and below the patient 350 and which are traversed by equal currents, especially in opposed directions. The first coil pair 210', 210" together are called selection means 210 in the following. Preferably, direct currents are used in this case. The selection means 210 generate a magnetic selection field 211 which is in general a gradient magnetic field which is represented in FIG. 2 by the field lines. It has a substantially constant gradient in the direction of the (e.g. vertical) axis of the coil pair of the selection means 210 and reaches the value zero in a point on this axis. Starting from this field-free point (not individually shown in FIG. 2), the field strength of the magnetic selection field 211 increases in all three spatial directions as the distance increases from the field-free point. In a first sub-zone 301 or region 301 which is denoted by a dashed line around the field-free point the field strength is so small that the magnetization of the magnetic particles 100 present in that first sub-zone 301 is not saturated, whereas the magnetization of the magnetic particles 100 present in a second sub-zone 302 (outside the region 301) is in a state of saturation. The field-free point or first sub-zone 301 of the region of action 300 is preferably a spatially coherent area; it may also be a punctiform area or else a line or a flat area. In the second sub-zone 302 (i.e. in the residual part of the region of action 300 outside of the first sub-zone 301) the magnetic field strength is sufficiently strong to keep the magnetic particles 100 in a state of saturation. By changing the position of the two sub-zones 301, 302 within the region of action 300, the (overall) magnetization in the region of action 300 changes. By measuring the magnetization in the region of action 300 or a physical parameter influenced by the magnetization, information about the spatial distribution of the magnetic particles 100 in the region of action can be obtained.

When a further magnetic field—in the following called a magnetic drive field 221 is superposed on the magnetic selection field 211 (or gradient magnetic field 211) in the region of action 300, the first sub-zone 301 is shifted relative to the second sub-zone 302 in the direction of this magnetic drive field 221; the extent of this shift increases as the strength of the magnetic drive field 221 increases. When the superposed magnetic drive field 221 is variable in time, the position of the first sub-zone 301 varies accordingly in time and in space. It is advantageous to receive or to detect signals from the magnetic particles 100 located in the first sub-zone 301 in another frequency band (shifted to higher frequencies) than the frequency band of the magnetic drive field 221 variations. This is possible because frequency components of higher harmonics of the magnetic drive field 221 frequency occur due to a change in magnetization of the magnetic particles 100 in the region of action 300 as a result of the non-linearity of the magnetization characteristics, i.e. the due to saturation effects.

In order to generate the magnetic drive field 221 for any given direction in space, there are provided three drive coil pairs, namely a first drive coil pair 220', a second drive coil pair 220" and a third drive coil pair 220''' which together are called drive means 220 in the following. For example, the first drive coil pair 220' generates a component of the magnetic drive field 221 which extends in a given direction, i.e. for example vertically. To this end the windings of the first drive coil pair 220' are traversed by equal currents in the same direction. The two drive coil pairs 220", 220''' are provided in order to generate components of the magnetic drive field 221 which extend in a different direction in space, e.g. horizontally in the longitudinal direction of the region of action 300 (or the patient 350) and in a direction perpendicular thereto. If second and third drive coil pairs 220", 220''' of the Helmholtz type were used for this purpose, these drive coil pairs would have to be arranged to the left and the right of the region of treatment or in front of and behind this region, respectively. This would affect the accessibility of the region of action 300 or the region of treatment 300. Therefore, the second and/or third magnetic drive coil pairs or coils 220", 220''' are also arranged above and below the region of action 300 and, therefore, their winding configuration must be different from that of the first drive coil pair 220'. Coils of this kind, however, are known from the field of magnetic resonance apparatus with open magnets (open MRI) in which a radio frequency (RF) drive coil pair is situated above and below the region of treatment, said RF drive coil pair being capable of generating a horizontal, temporally variable magnetic field. Therefore, the construction of such coils need not be further elaborated herein.

The arrangement 10 according to the present invention further comprise receiving means 230 that are only schematically shown in FIG. 1. The receiving means 230 usually comprise coils that are able to detect the signals induced by the magnetization pattern of the magnetic particle 100 in the region of action 300. Coils of this kind, however, are known from the field of magnetic resonance apparatus in which e.g. a radio frequency (RF) coil pair is situated around the region of action 300 in order to have a signal to noise ratio as high as possible. Therefore, the construction of such coils need not be further elaborated herein. According to the present invention, it is preferred that the resistance of the receiving means is dominated by thermal noise, especially generated by thermal noise due to the presence of the magnetic particles in the region of action, i.e. the resistance of the current supporting paths without the presence of the magnetic particles in the region of action is comparable or smaller than the resistance in presence of the magnetic particles in the region of action. This is achieved in particular by means of carefully defining the individual current paths, current strength, wire configuration and other characteristics of the receiving means.

Such an arrangement and such a method of detecting magnetic particles are known from DE 101 51 778 which is hereby incorporated in its entirety.

According to the present invention, the used magnetic particles 100 have an anisotropy of their magnetization. If mono domain magnetic particles having an anisotropy of their magnetization are exposed to an external magnetic field, the response of the magnetic particles depend on the direction of the field with respect to the direction of easy magnetization (easy axis). If the external magnetic field is perpendicular to the easy axis, the response signal is comparably low. If the external magnetic field is parallel to the easy axis, the response signal is much larger. Astonishingly, the signal is optimal if the external magnetic field that the magnetic particles 100 experience (i.e. for the first sub-zone 301 of the region of action 300, the external magnetic field corresponds to the magnetic drive field 221) is oriented in a specific angle relative to the easy axis of the magnetic particle 100. This is shown in an example in FIG. 3.

Figure 3:
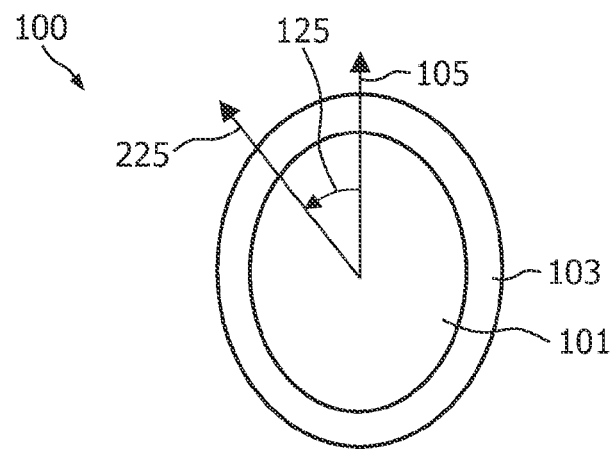
FIG. 3 illustrates an enlarged view of a magnetic particle present in the region of action.

FIG. 3 shows an example of a magnetic particle 100 of the kind used together with an arrangement 10 of the present invention. It comprises for example a mono domain magnetic material 101, e.g. of the ferromagnetic type. This magnetic material 101 may be covered, for example, by means of a coating layer 103 which protects the particle 100 against chemically and/or physically aggressive environments, e.g. acids. The magnetic field strength of the magnetic selection field 211 required for the saturation of the magnetization of such particles 100 is dependent on various parameters, e.g. the diameter of the particles 100, the used magnetic material 101 and other parameters. According to the present invention, the magnetic particles 100 are magnetically anisotropic, i.e. they have an anisotropy of their magnetization. Such an anisotropy can e.g. be provided by means of shape anisotropy and/or by means of crystal anisotropy and/or by means of induced anisotropy and/or by means of surface anisotropy. The magnetic particle 100 comprises a direction of easy magnetization, also called easy axis 105. The magnetic drive field 220 produces at the location of the first sub-zone 301 a magnetic drive vector 225 corresponding to the direction of the external magnetic field that the magnetic particle 100 experiences. According to the present invention, the magnetic drive vector 225 should be oriented with a relatively high probability in a special angle 125 relative to the direction of easy magnetization 105 of the magnetic particle 100. Thereby, the magnetization signal of the magnetic particle 100 is enhanced.

Figure 6:
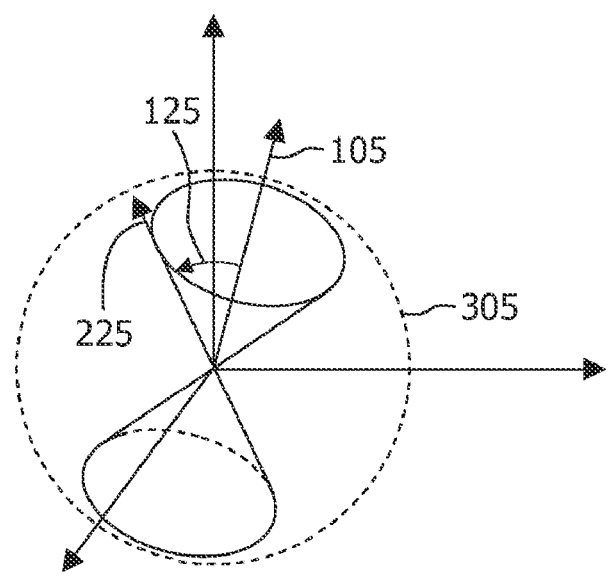
FIG. 6 illustrates schematically a representation of the field of view.

According to preferred embodiments of the present invention, this can be realized by means of special signal sequences applied to the drive means 220 such that the magnetic drive vector 225 moves in a special manner trough the so-called field of view, i.e. inside the area of the region of action 300 where the comparably quickly changing magnetic drive field 220 interacts with the magnetic particles 100. In FIG. 6, the field of view is represented by a sphere and the reference sign 305. Furthermore, FIG. 6 shows an example of the movement of the drive vector 225 in a drive sequence according to the present invention. The magnetic drive vector 225 is moved quickly along the double cone structure (i.e. the magnetic drive vector moves on the surface of the cone) depicted in FIG. 6. As the magnetic particles 100 cannot follow the movement of the drive vector 225, the mean direction of the magnetic drive vector 225 is along the center of the cone, i.e. the first direction is parallel to the easy axis 105 of the magnetic particles 100 as represented by the arrow 105 in FIG. 6. When the orientation of drive vector 225 is periodically reversed (e.g. from being oriented in the direction of the upper cone towards the direction of the lower cone), the magnetic particles 100 experience the magnetic drive vector 225 along the second direction being inclined relative to the first direction by the special angle 125. Thereby, it is possible to enhance the signal generated by the magnetic particles 100. In order to cover the complete field of view 305, the double cone can be rotated at a comparably low rate such that gradually all the magnetic particles 100 inside the field of view 305 contribute in generating the enhanced signal.

In the example shown in FIG. 3, the anisotropy of the magnetic particle 100 is provided by means of shape anisotropy. The magnetic particle 100 is quasi spherical, only along the direction of it longest extension (also called z-direction; in FIG. 3 the up-down-direction) it is longer than in the two directions (also called x-direction and y-direction) of the plane perpendicular to its longest extension. For example, the longest extension of the magnetic particle 100 is 31 nm and the extension in the two other directions (x- and y-direction) of the magnetic particle 100 is 30 nm. In the context of the present invention, the dimensions given of the magnetic particles 100 correspond to the dimensions of the magnetic material 101 of the magnetic particles 100.

According to the present invention, it is preferred to use a well defined strength of anisotropy of the magnetization of the magnetic particles 100 of about 1 mT to about 10 mT, preferably of about 3 mT to about 5 mT. In the example given, this strength of anisotropy could be exceeded if the shape anisotropy would be enhanced to a length of the particles (along their longest direction) of 32 nm while still having a diameter in the other directions (x- and y-directions) of 30 nm. This is also represented in FIG. 5.

Figure 5:
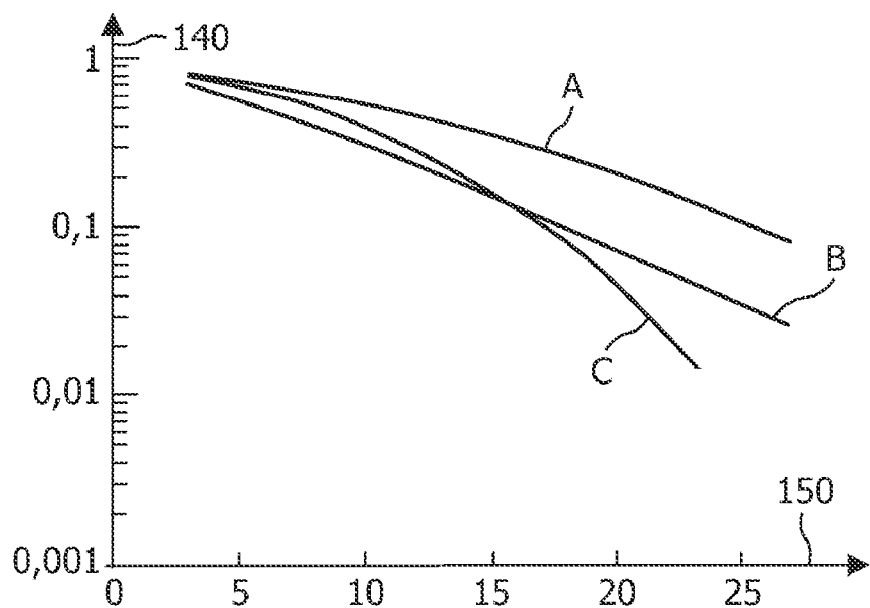
FIG. 5 illustrates schematically a diagram of the relative signal strength of three kinds of magnetic particles.

FIG. 5 represents diagrams of the relative signal strength 140 of magnetic particles 100 of three different shapes. The relative signal strength 140 is shown for several harmonics of different order 150. For all three particles, the signal strength 140 decreases when the ordinal number of harmonic increases. Nevertheless, the decrease in signal strength 140 is smaller for the magnetic particles 100 represented by the curve A than the magnetic particles 100 represented by the curves B and C. The curve A corresponds to magnetic particles 100 having a shape anisotropy due to their extension in the x-, y- and z-direction of 30 nm, 30 nm and 31 nm respectively. The curve B corresponds to magnetic particles 100 having a shape anisotropy due to their extension in the x-, y- and z-direction of 30 nm, 30 nm and 30 nm respectively. The curve C corresponds to magnetic particles 100 having a shape anisotropy due to their extension in the x-, y- and z-direction of 30 nm, 30 nm and 32 nm respectively. The best relative signal strength 140 is therefore achieved with the magnetic particles corresponding to the curve A.

In order to generate the magnetic drive field 221 such that the magnetic drive vector 225 is rotated in at least one rotation plane, the first, second and third drive coil pair 220', 220", 220''' are controlled such that the resulting vector of the magnetic strength in the first sub-zone 301 (i.e. the overall magnetic strength vector (=magnetic drive vector 225) produced both by the selection field 211 and by the drive field 221) which corresponds to the external magnetic field experienced by the magnetic particles 100 is rotating, e.g. by applying an additional time-varying frequency to the control signal of the drive coil pairs 220', 220", 220'''. This is especially done by means of a control unit controlled by a computer program. The computer program is especially stored on a data carrier provided inside the control unit or assigned to the control unit. The data carrier might either be removable from the control unit or be placed statically inside the control unit or assigned thereto.

Figure 4A:
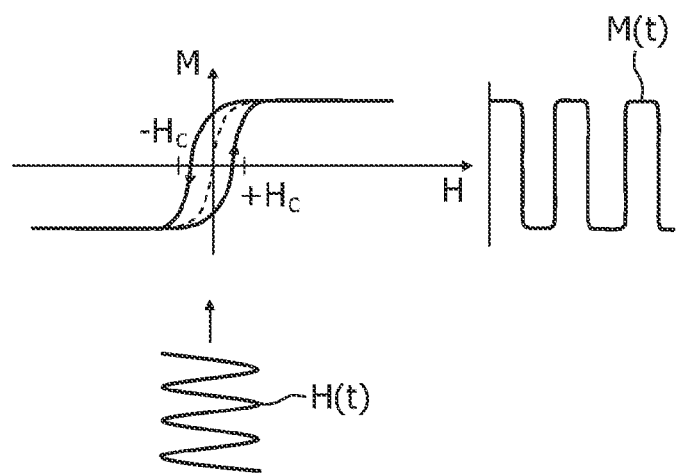
FIGS. 4a and 4b illustrate the magnetization characteristics of such particles.
Figure 4B:
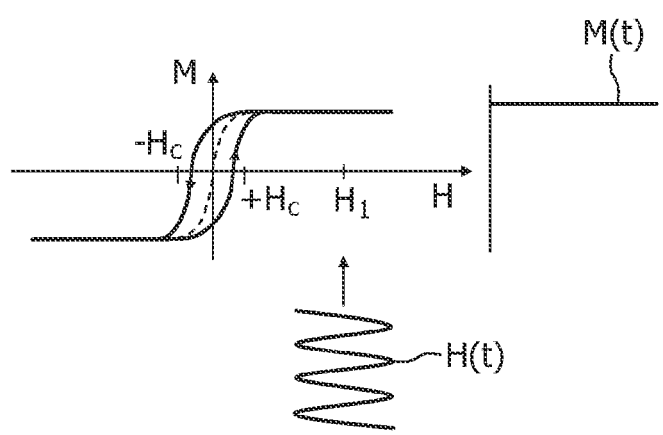

FIGS. 4a and 4b show the magnetization characteristic, that is, the variation of the magnetization M of a part of the magnetic particles 100 (not shown in FIGS. 4a and 4b) as a function of the field strength H at the location of that part of the magnetic particle 100. It appears that the magnetization M no longer changes beyond a field strength $+H_c$ and below a field strength $-H_c$, which means that a saturated magnetization is involved. The magnetization M is not saturated between the values $+H_c$ and $-H_c$.

FIG. 4a illustrates the effect of a sinusoidal magnetic field H(t) on a part of the magnetic particles 100 where the absolute values of the resulting sinusoidal magnetic field H(t) (i.e. "seen by the magnetic particles 100") are lower than the magnetic field strength required to saturate the magnetic particles 100, i.e. in the case where no further magnetic field is active. The magnetization of the magnetic particles 100 reciprocates between its saturation values at the rhythm of the frequency of the magnetic field H(t). The resultant variation in time of the magnetization is denoted by the reference M(t) on the right hand side of FIG. 4a. It appears that the magnetization also changes periodically and that the magnetization of the magnetic particles 100 is periodically reversed.

The dashed part of the line at the centre of the curve denotes the approximate mean variation of the magnetization M(t) as a function of the field strength of the sinusoidal magnetic field H(t). As a deviation from this centre line, the magnetization extends slightly to the right when the magnetic field H increases from $-H_c$ to $+H_c$ and slightly to the left when the magnetic field H decreases from $+H_c$ to $-H_c$.

FIG. 4b shows the effect of a sinusoidal magnetic field H(t) on which a further magnetic field $H_1$ (having a frequency that is small relative to the frequency of the sinusoidal magnetic field H(t)) is superposed. Because the magnetization is in the saturated state, it is practically not influenced by the sinusoidal magnetic field H(t). The magnetization M(t) remains constant in time at this area. Consequently, the magnetic field H(t) does not cause a change of the state of the magnetization.

The invention claimed is:

1. A method for influencing at least one of and detecting magnetic particles in a region of action, wherein the method comprises the steps of generating a magnetic selection field having a pattern in space of its magnetic field strength such that a first sub-zone having a low magnetic field strength and a second sub-zone having a higher magnetic field strength are formed in the region of action;

changing position in space of the first sub-zone and the second sub-zone in the region of action by applying a control signal to at least one pair of coils to generate a magnetic drive field to locally change magnetization of the magnetic particles, wherein the control signal is variable in time;

acquiring signals that depend on the magnetization in the region of action, wherein the magnetization is influenced by the change in the position in space of the first sub-zone and the second sub-zone, wherein a magnetic drive vector of the magnetic drive field is rotated in at least one rotation plane by applying a time-varying frequency signal to the control signal to orient the magnetic particles with their easy axis along a first direction in a first step, and in a second step to direct the magnetic drive vector is along a second direction inclined at an angle relative to the first direction.

2. The method according to claim 1, wherein the rotation of the magnetic drive vector of the magnetic drive field is performed continuously during the acquisition of the signals.

3. The method according to claim 1, wherein the plane of rotation of the magnetic drive vector of the magnetic drive field is also rotated during the rotation of the magnetic drive vector of the magnetic drive field by applying a further control signal to the at least one pair of coils.

4. The method according to claim 1, wherein the rotation of the magnetic drive vector of the magnetic drive field is made at a frequency of about 100 Hz to about 100 kHz.

5. The method according to claim 4, wherein the frequency of the rotation of the magnetic drive vector of the magnetic drive field is in the range of the frequency of rotation of the magnetic particles in their environment.

6. The method according to claim 4, wherein the frequency of the rotation of the magnetic drive vector of the magnetic drive field is changed such that the signal to noise ratio of the acquired signal is optimal.

7. The method according to claim 1, wherein magnetic particles are used having an anisotropy of their magnetization.

8. The method according to claim 7, wherein the strength of anisotropy of the magnetization is in a range of about 1 mT to about 10 mT.

9. The method according to claim 7, wherein the anisotropy of the magnetization is due to at least one of shape anisotropy, crystal anisotropy, induced anisotropy and surface anisotropy.

10. The method according to claim 7, wherein the rotation of the magnetic drive vector of the magnetic drive field is performed such that the magnetic drive vector of the magnetic drive field is oriented with a relatively high probability in an angle relative to the direction of easy magnetization of the magnetic particles, wherein the angle is in a range of about 20° to about 70°.

11. The method according to claim 7, wherein the strength of anisotropy of the magnetization is in a range of about 3 mT to about 5 mT.

12. The method according to claim 7, wherein the rotation of the magnetic drive vector of the magnetic drive field is performed such that the magnetic drive vector of the magnetic drive field is oriented with a relatively high probability in an angle relative to the direction of easy magnetization of the magnetic particles, wherein the angle is in a range of about 30° to about 60°.

13. An arrangement for at least one of influencing and detecting magnetic particles in a region of action, wherein the arrangement comprises:

selection means for generating a magnetic selection field having a pattern in space of its magnetic field strength such that a first sub-zone having a low magnetic field strength and a second sub-zone having a higher magnetic field strength are formed in the region of action;

drive means for changing position in space of the first sub-zone and the second sub-zone in the region of action by applying a control signal to at least one pair of coils to generate a magnetic drive field to locally change magnetization of the magnetic particles wherein the control signal is variable in time;

receiving means for acquiring signals that depend on the magnetization in the region of action, wherein the magnetization is influenced by the change in the position in space of the first sub-zone and the second sub-zone, wherein a magnetic drive vector of the magnetic drive field is rotated in at least one rotation plane by applying a time-varying frequency signal to the control signal to orient the magnetic particles with their easy axis along a first direction in a first step, and in a second step to direct the magnetic drive vector is along a second direction inclined at an angle relative to the first direction.

14. The arrangement according to claim 13, wherein the rotation of the magnetic drive vector of the magnetic drive field is made at a frequency of about 100 Hz to about 100 kHz.

15. A non-transitory computer readable medium embodying computer instructions which, when executed by a processor, configure the processor to perform a method for at least one of influencing and detecting magnetic particles in a region of action, the method comprising the acts of:

generating a magnetic selection field having a pattern in space of its magnetic field strength such that a first sub-zone having a low magnetic field strength and a second sub-zone having a higher magnetic field strength are formed in the region of action;

changing position in space of the first sub-zone and the second sub-zone in the region of action by applying a control signal to at least one pair of coils to generate a magnetic drive field to locally change magnetization of the magnetic particles, wherein the control signal is variable in time;

acquiring signals that depend on the magnetization in the region of action, wherein the magnetization is influenced by the change in the position in space of the first sub-zone and the second sub-zone, wherein a magnetic drive vector of the magnetic drive field is rotated in at least one rotation plane by applying a time-varying frequency signal to the control signal to orient the magnetic particles with their easy axis along a first direction in a first step, and in a second step to direct the magnetic drive vector is along a second direction inclined at an angle relative to the first direction.

* * * * *